United States Patent
Amblard et al.

(10) Patent No.: US 9,526,901 B2
(45) Date of Patent: *Dec. 27, 2016

(54) ACTIVE IMPLANTABLE MEDICAL DEVICE FOR ATRIAL STIMULATION FOR THE TREATMENT OF HEART FAILURE WITH PRESERVED EJECTION FRACTION

(71) Applicant: SORIN CRM SAS, Clamart (FR)

(72) Inventors: Amel Amblard, Sceaux (FR); Marcel Limousin, Paris (FR)

(73) Assignee: SORIN CRM SAS, Clamart (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/067,941

(22) Filed: Mar. 11, 2016

(65) Prior Publication Data

US 2016/0193470 A1    Jul. 7, 2016

Related U.S. Application Data

(63) Continuation of application No. 14/541,717, filed on Nov. 14, 2014, now Pat. No. 9,283,393.

(30) Foreign Application Priority Data

Nov. 15, 2013    (FR) ..................... 13 61199

(51) Int. Cl.
*A61N 1/00* (2006.01)
*A61N 1/365* (2006.01)
(Continued)

(52) U.S. Cl.
CPC ......... *A61N 1/36592* (2013.01); *A61N 1/3627* (2013.01); *A61N 1/3684* (2013.01)

(58) Field of Classification Search
CPC A61N 1/36592; A61N 1/3627; A61N 1/3684; A61N 1/3622; A61N 1/3624
See application file for complete search history.

(56) References Cited

U.S. PATENT DOCUMENTS 6,941,170 B1    9/2005  Lu
7,308,306 B1    12/2007 Park et al.
(Continued)

FOREIGN PATENT DOCUMENTS

EP    2 471 575    7/2012

OTHER PUBLICATIONS

Foreign Search Report for French Patent Application No. FR 1361199, dated Jan. 30, 2014, 2 pages.

*Primary Examiner* — Mallika D Fairchild
(74) *Attorney, Agent, or Firm* — Foley & Lardner LLP

(57) ABSTRACT

An active implantable medical device includes digital processor circuits configured to sense right and left atrial depolarizations and deliver left atrial stimulation pulses according to a stimulation protocol. The stimulation protocol includes delivering a left atrial stimulation pulse at an inter-atrial coupling interval. The inter-atrial coupling interval is a coupling interval shorter than the sinus rhythm coupling interval, so as to deliver a premature pulse. The protocol further includes delivering a not premature left-atrial stimulation pulse during an immediately subsequent cardiac cycle, at an inter-atrial coupling interval corresponding to the sinus rhythm coupling interval. The protocol also includes assessing the right atrial coupling interval between the right atrial depolarizations and comparing the right atrial coupling interval to the sinus rhythm coupling interval. And finally, modifying an adjustable controlling parameters if necessary according to the result of the comparison. The device has no means for collecting and analyzing the endocardial acceleration.

20 Claims, 4 Drawing Sheets

(51) Int. Cl.
*A61N 1/362* (2006.01)
*A61N 1/368* (2006.01)

(56) References Cited

U.S. PATENT DOCUMENTS 7,474,921 B1 1/2009 Bornzin et al.
7,494,921 B2 2/2009 Han

ACTIVE IMPLANTABLE MEDICAL DEVICE FOR ATRIAL STIMULATION FOR THE TREATMENT OF HEART FAILURE WITH PRESERVED EJECTION FRACTION

CROSS REFERENCE TO RELATED APPLICATIONS

This application is a continuation of U.S. application Ser. No. 14/541,717, filed Nov. 14, 2014, which claims the benefit of and priority to French Application No. 1361199, filed Nov. 15, 2013, both of which are hereby incorporated by reference herein in their entireties.

BACKGROUND

The invention relates to "active implantable medical devices" as defined by Directive 90/385/EEC of 20 Jun. 1990 of the Council of the European Communities, specifically implants to continuously monitor heart rhythm and deliver if necessary electrical pulses to the heart for stimulation, resynchronization and/or defibrillation in case of rhythm disorder detected by the device. It more particularly relates to devices for treating heart failure (HF), as an alternative or in addition to the treatment of cardiac rhythm disorders.

This therapy is designed to resynchronize the contraction of the heart chambers (atrium and ventricle) so as to improve the patient's condition by optimizing the phases of the hemodynamic cycle. The cycle includes pre-ejection, isovolumetric contraction, systolic ejection, isovolumetric relaxation and finally filling of the cavity.

Most of these devices implement a technique called "CRT" (Cardiac Resynchronization Therapy) or "BVP" (Bi-Ventricular Pacing) for delivering, as necessary, electrical pulses needed to ensure joint and continuous stimulation of the two (left and right) ventricles to resynchronize them. This biventricular resynchronization technique however addresses only one of the forms of heart failure, known as "systolic failure". In this form of the disease, the heart muscle is unable to provide the force necessary to ensure adequate cardiac output, and the patient shows signs of expansion resulting in a delay of left ventricular depolarization. CRT biventricular pacing is then used to resynchronize the ventricles and make more uniform cardiac contraction.

In the other form of heart failure called "diastolic failure" or "preserved ejection fraction heart failure" (HFpEF, Heart Failure with preserved Ejection Fraction), there is no desynchronization of the ventricles; it comes from a failure in the left ventricular filling. Biventricular CRT stimulation will be ineffective in this case. This condition affects about 40% of heart failure patients, and there is no known effective treatment to remedy to it.

This form of disease in some patients may be the result of a disorder of conduction in the atria (inter-atrial block), which delays the depolarization, and therefore the contraction of the left atrium (OG) with respect to the right atrium (OD). However, as atrioventricular conduction pathways are not altered, depolarization and contraction of the right (VD) and left (VG) ventricles occur within a reasonable time, without synchronization VD-VG. It is between the contraction of the left atrium and that of the left ventricle that the inter-atrial block OD-OG generates a poor sequencing OG-VG. The delay of the contraction of the left atrium has for consequence that it contracts substantially at the same moment as the left ventricle, and therefore cannot properly fulfill its function and contribute to the left ventricular active filling.

To treat this heart failure with preserved ejection fraction, a technique of atrial overdriving, pathology, has been proposed. This is described for example in the U.S. Pat. No. 7,494,921B1, which describes permanently stimulating the left atrium to a frequency slightly above the spontaneous sinus rhythm frequency (i.e. the rate of the right atrium), thereby systematically causing premature depolarization of the left atrium and restoring an almost normal OG-VG sequence.

Specifically, in this technique, the device regularly measures the spontaneous rhythm of the patient and applies a sequence of pacing pulses at a slightly faster rate, arbitrarily programmed to cause a prematurity in the order of 50 to 100 ms compared to an atrial coupling interval corresponding to the spontaneous sinus rhythm. After several cycles at this accelerated pace, the frequency gradually slows until reappearance of spontaneous activity, then the overdriving method is repeated in the same way.

In the description of this technique, the "atrial coupling interval" or "atrial coupling" is defined as the time interval separating two spontaneous (in sinus rhythm, also designated as "PP interval") or stimulated consecutive atrial events. The applied stimulation frequency thus varies continuously between values wherein it is too fast (overdriving period) or too slow (period of reappearance of spontaneous rhythm, with OD-VD synchronization), without real monitoring of the effectiveness of a possible return to a proper synchronization of the left cavities.

It should also be noted that this pacing mode may interfere with the filling of the right cavities. In fact, due to premature stimulation of the left atrium, the OD-VD synchronization is significantly altered in a manner which may be incompatible with satisfactory filling of the right ventricle (we will clarify these aspects in the detailed description). Improvement therapy in left ventricular filling is thus likely to induce adverse effects on the filling of the right ventricle, so in the cavity that was not affected by the pathology to be treated.

Moreover, this technique requires the presence of a right ventricular sensing lead, so as to ensure that overdriving is controlled on the basis of the actual atrial activity, and not on signals detected at the atrium but actually due to the depolarization of the ventricles (far-field signals).

Another technique is described in EP 2471575 A1 (Sorin CRM SAS) which implements a sensor for collecting an endocardial acceleration signal (EA). The EA signal is analyzed to detect the presence of a specific component reflecting atrial contraction (EA4 component) and to identify the instant of occurrence of this component. If the EA4 component is present, this means that the sequencing of atrial contractions is correct because otherwise (i.e., left atrial contractions too late), the EA4 component would be mixed in the component of the EA signal corresponding to the immediately following ventricular contraction (EA1 component). The atrial stimulation interval (AA interval) is then dynamically adjusted depending on the result of this analysis.

However, this technique requires an implantable lead provided with an endocardial acceleration sensor, and a generator capable of processing the EA signals delivered by such a sensor.

SUMMARY

One object of the invention is to propose a new technique for treatment of heart failure with preserved ejection fraction in patients with mechanical inter-atrial delay, which overcomes the drawbacks of the methods proposed so far and which does not require the use of methods for collecting and analyzing an EA signal.

Another object of the invention is to propose a technique that ensures recovery of diastolic function in a method that is relatively simple (in terms of resources used) and reactive (high efficiency obtained cycle to cycle).

The invention operates by a unique atrial pacing to restore a satisfactory OG-VG sequencing (sequencing the contraction of the left atrium compared to that of the left ventricle), so that the atrium can properly fulfill its function of completion of the filling of the left ventricle.

To implement the disclosed embodiments, there is no need for ventricular pacing and/or ventricular depolarization detection methods. The latter can of course exist, for example in the case of a multi-site pacemaker providing stimulation of the right ventricle or of the two ventricles in addition to the stimulation of the atria (triple or quadruple chamber pacemakers). But these ventricular methods are not involved in the treatment of heart failure with preserved ejection fraction, which aims to overcome pre-existing conduction condition between the atria, namely an inter-atrial block resulting in an excessive delay in conduction between the right atrium and the left atrium.

Specifically, the invention provides a device including digital processor circuits configured for: sensing of right atrial depolarizations; sensing of left atrial depolarizations; delivering left atrial stimulation pulses; and delivering, selectively on the basis of adjustable controlling parameters, of premature the left atrial stimulation pulses, by applying a short inter-atrial coupling, shorter than the sinus rhythm coupling interval A feature of the invention is that the device has no means for collecting and analyzing the endocardial acceleration, and the digital processor is configured so as to:
 after a first cardiac cycle without left atrial stimulation, deliver a left atrial stimulation pulse during an immediately consecutive second cardiac cycle, with application of an inter-atrial coupling,
 the inter-atrial coupling applied during the second immediately consecutive cardiac cycle being a short coupling shorter than the sinus rhythm coupling interval, so that the left atrial stimulation pulse delivered during the second cardiac cycle is a premature pulse;
 deliver a not premature left-atrial stimulation pulse during a third cardiac cycle immediately subsequent to the second cardiac cycle, with application of an inter-atrial coupling corresponding to the sinus rhythm coupling interval (D1), so as to:
  assess the right atrial coupling interval between the right atrial depolarizations during the second and third cardiac cycles;
  compare the right atrial coupling interval thus assessed to the sinus rhythm coupling interval; and
 modify or not, at least one of the adjustable controlling parameters according to the result of the comparison.

According to various advantageous subsidiary characteristics:
 the modified or not controlling parameter depending on the result of the comparison is the short inter-atrial coupling;
 in that case, if the right atrial coupling interval is less than the sinus rhythm coupling interval (D1), the digital processor is further configured so as to change by one step the short inter-atrial coupling, then deliver a premature left atrial stimulation pulse during a subsequent cardiac cycle, with application of the short inter-atrial coupling changed by one step;
 on detection of a predetermined event, the digital processor is further configured so as to
  inhibit any delivery of left atrial stimulation pulse during at least one cardiac cycle;
  measure on at least one cardiac cycle the atrial escape interval and the inter-atrial delay;
  and store this escape interval as a coupling interval of the sinus rhythm for the determination of the short inter-atrial coupling and inter-atrial delay corresponding to the sinus rhythm coupling interval in the subsequent cycles;
 the predetermined event is the expiry of a predetermined fixed timing interval; and
 the predetermined event is the detection of the crossing of a predetermined threshold by the variation in the atrial coupling interval.

According to one embodiment, there is an active implantable medical device, the device comprising digital processor circuits configured to sense right and left atrial depolarizations and deliver, selectively on the basis of adjustable controlling parameters, left atrial stimulation pulses according to a stimulation protocol. The stimulation protocol includes, after a first cardiac cycle without left atrial stimulation, delivering a left atrial stimulation pulse during an immediately consecutive second cardiac cycle at an inter-atrial coupling interval. The inter-atrial coupling interval applied during the second immediately consecutive cardiac cycle is a short coupling interval shorter than the sinus rhythm coupling interval, so that the left atrial stimulation pulse delivered during the second cardiac cycle is a premature pulse. The protocol further includes delivering a not premature left-atrial stimulation pulse during a third cardiac cycle immediately subsequent to the second cardiac cycle, at an inter-atrial coupling interval corresponding to the sinus rhythm coupling interval. The protocol also includes assessing the right atrial coupling interval between the right atrial depolarizations during the second and third cardiac cycles and comparing the right atrial coupling interval to the sinus rhythm coupling interval. And finally, modifying at least one of the adjustable controlling parameters if necessary according to the result of the comparison. The device has no means for collecting and analyzing the endocardial acceleration.

According to another embodiment, there is a method for resynchronization of the contraction of the heart chambers. The method includes sensing right atrial depolarizations and sensing left atrial depolarizations. The method also includes delivering, selectively on the basis of adjustable controlling parameters, left atrial stimulation pulses according to a stimulation protocol. The stimulation protocol includes, after a first cardiac cycle without left atrial stimulation, delivering a left atrial stimulation pulse during an immediately consecutive second cardiac cycle at an inter-atrial coupling interval. Thei nter-atrial coupling interval applied during the second immediately consecutive cardiac cycle is a short coupling interval shorter than the sinus rhythm coupling interval, so that the left atrial stimulation pulse delivered during the second cardiac cycle is a premature pulse. The protocol further includes delivering a not premature left-atrial stimulation pulse during a third cardiac cycle immediately subsequent to the second cardiac cycle, at an inter-atrial coupling interval corresponding to the sinus rhythm coupling interval; and assessing the right atrial coupling interval between the right atrial depolarizations during the second and third cardiac cycles. The protocol also includes comparing the right atrial coupling interval to the sinus rhythm coupling interval and modifying at least one of the adjustable controlling parameters if necessary according to the result of the comparison.

According to yet another embodiment, there is a cardiac resynchronization system including a stimulation/detection electrode for positioning in the right atrium of a heart and a stimulation/detection electrode for positioning in the left atrium of the heart, wherein the electrodes are configured to be coupled to an implantable medical device. The implantable medical device includes a generator and digital processor circuits. The digital processor circuits are configured to sense right atrial depolarizations from the stimulation/detection electrode and sense left atrial depolarizations from the stimulation/detection electrode. The digital processor circuits are further configured to deliver a left atrial stimulation pulse during a cardiac cycle immediately following a preceding cardiac cycle with no left atrial stimulation, the left atrial stimulation pulse delivered at an inter-atrial coupling interval. The inter-atrial coupling interval is a short coupling interval shorter than the sinus rhythm coupling interval. The digital processor circuits are further configured to deliver a second left-atrial stimulation pulse during an immediately subsequent cardiac cycle at an inter-atrial coupling interval corresponding to the sinus rhythm coupling interval. The digital processor circuits are further configured to assess the right atrial coupling interval between the right atrial depolarizations during the consecutive cardiac cycles and compare. the right atrial coupling interval to the sinus rhythm coupling interval. After comparing, the digital processor circuits are configured to determine whether to modify the inter-atrial coupling interval based on the result of the comparison.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 schematically illustrates the position of the different sites involved in the cyclic, spontaneous or stimulated, electrical activity of the heart.

DETAILED DESCRIPTION

Regarding its software aspects, the invention may be implemented by appropriate programming of the controlling software of a known stimulator, for example a cardiac pacemaker, resynchronizer or defibrillator, including methods of acquisition of a signal provided by endocardial leads. The invention may notably be applied to implantable devices, such as that of the Reply, Ovatio and Paradym families, manufactured and commercialized by Sorin CRM, Clamart, France.

These devices include programmable microprocessor circuitry to receive, format and process electrical signals collected by implantable electrodes, and deliver stimulation pulses to these electrodes. It is possible to download in it by telemetry software that is stored in memory and executed to implement the functions of the invention that are described below. The adaptation of these devices to the implementation of the functions of the invention is within the skill in the art and will not be described in detail.

Figure 1:
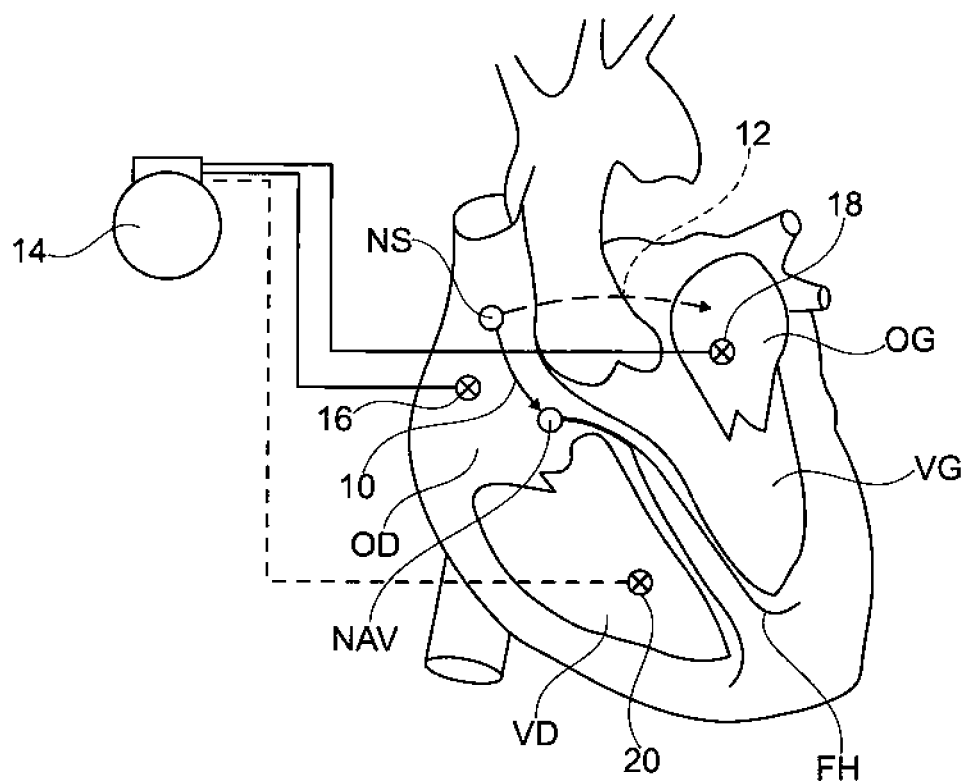

FIG. 1 shows a diagram of the heart with its four chambers: right atrium OD, right ventricle VD, left atrium OG and left ventricle VG. The coordinated contraction of the different cavities is originated in the sinus node NS, then the depolarization wave is conducted to the atrioventricular node NAV (conduction represented by arrow 10), then from this node to the His bundle FH, and finally to tissues of right and left ventricles VD and VG, causing contraction thereof. Moreover, the depolarization wave originated from the sinus node NS causes contraction of the right atrium OD and, after inter-atrial conduction (conduction represented by arrow 12) to the left atrium, causes contraction of the latter.

In the case of a patient suffering from heart failure with preserved ejection fraction, the atrioventricular conduction (arrow 10, from the sinus node NS to the atrioventricular node NAV) is usually preserved, as well as the conducting paths to ensure synchronous contraction of both the left (VG) and right (VD) ventricles. However, when atrial conduction (arrow 12) is altered, it causes a delay in the depolarization and therefore in the contraction of the left atrium OG compared to the ventricles. This induces a poor timing of the contraction of the left atrium OG relative to the left ventricle VG, with a substantially concomitant contraction of the two cavities. Therefore, the left atrium OG cannot properly fulfil its function, which is to complete the filling of the left ventricle VG.

The implantable device 14 includes a generator connected to a stimulation/detection electrode 16 at the right atrium OD, and a stimulation/detection electrode 18 at the left atrium OG. The electrode 18 may be positioned in particular in the coronary sinus or in a vein belonging to the coronary network such as the Marshall vein, or on the inter-atrial septum, or directly into the left atrium after puncture of the inter-atrial septum. In a particular implementation described at the end of the present description, or for purposes other than implementation of the invention, the device may also include a ventricular lead 20 such as an endocardial lead implanted in the right ventricle VD.

Figure 2:
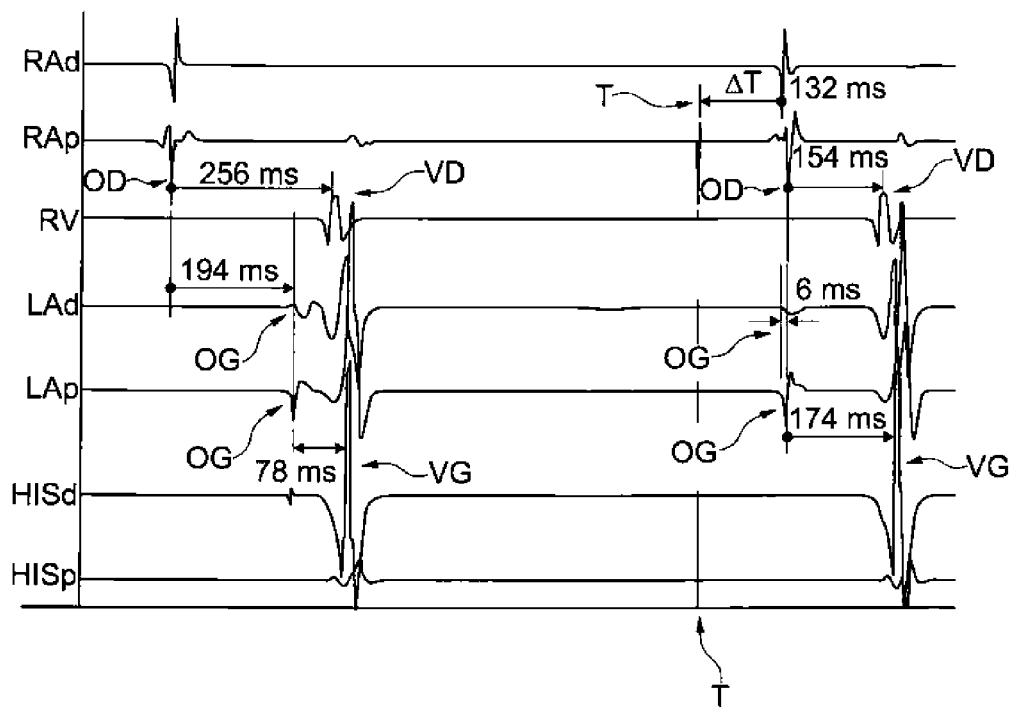
FIG. 2 is a series of timing diagrams illustrating various signals characterizing cardiac activity during two successive cycles, in the case of a known overdriving technique.

The overdriving conventional technique usually implemented with this type of device to remedy a heart failure with preserved ejection fraction is illustrated in FIG. 2. Plots of various records collected during two successive cardiac cycles are shown in this figure: the first in spontaneous rhythm, the second with overdriving. These records correspond to the following branches: distal and proximal electrodes on the right atrium (RAd and RAp), right ventricle (RV), distal and proximal electrodes on the left atrium (LAd and LAp), and distal and proximal electrodes on the His bundle (HISd and HISp), roughly corresponding to the depolarization of the left ventricle (including the HISd branch).

At the first cardiac cycle there is a delay, compliant, of 256 ms between the spontaneous depolarization of the right ventricle (VD) and the depolarization of the right atrium (OD). By contrast, the OD-OG delay between the respective depolarization of both atria has an excessive and pathological value of 194 ms, which has the effect of leaving a gap of 78 ms between the depolarization of the left atrium (OG) and the contraction of the left ventricle (VG), an interval too short to provide adequate filling of the left ventricle. In extreme cases, the contraction of the left atrium and of the left ventricle can even be almost concurrent, negating the role of the atrium in the filling of the ventricle.

In the second cardiac cycle, which is a cycle with overdriving, the device paces the left atrium at a given time (T) having a deliberate prematurity ΔT from the normal sinus rhythm interval corresponding to the cycle to cycle coupling interval OD-OD. This premature stimulation of the left atrium will restore an almost physiological sequencing OG-VG (174 ms). However, the OD-VD sequencing is significantly changed, since this delay is now 154 ms instead of 256 ms, which may result in deleterious effects regarding the right cavity hemodynamic.

Figure 3:
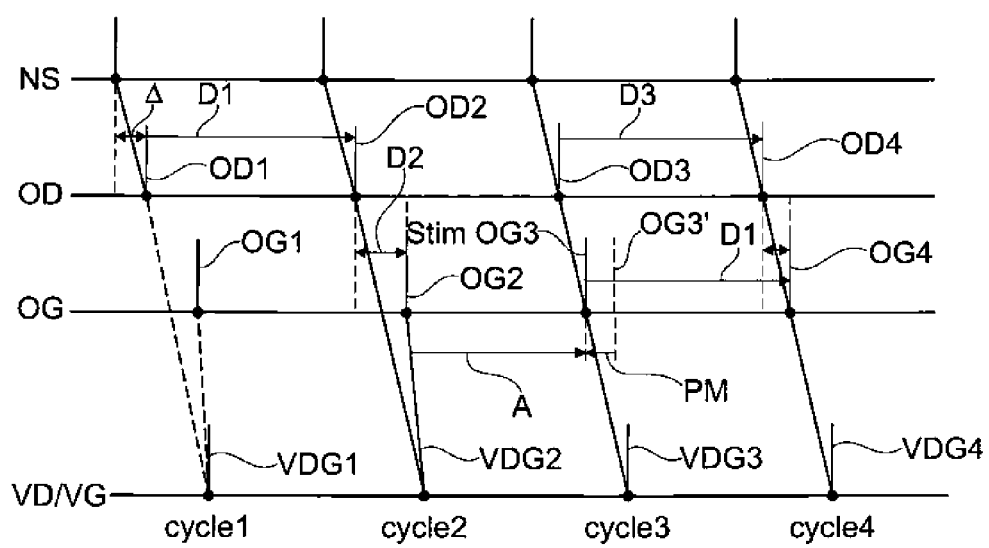
FIG. 3 is a diagram illustrating, in one exemplary embodiment, the sequencing of atrial and ventricular detections and stimulations in four successive cardiac cycles, in the case of a device operating according to the teachings of the invention.

FIG. 3 is a diagram illustrating the sequencing of atrial and ventricular detections and stimulations during four successive cardiac cycles, in the case of a device operating according to the teachings of the invention. On this diagram are represented various markers corresponding to the sinus rhythm NS, to the right atrial rhythm OD, to the left atrial rhythm OG, and to the ventricular rhythm VD/VG (it is assumed that there is no delay between the depolarization of the right ventricle and that of the left ventricle).

The basic principle of the invention is to control the device with stimulation of the left atrium, controlled to avoid any overdriving effect and thus not to change the right atrioventricular sequence. Initially (Cycle 1), the initial influx originated from the sinus node spreads through the right atrium. The OD1 marker corresponds to the detection by the right atrial lead with a delay Δ from the beginning of the cycle, a delay corresponding to the propagation delay to the right atrium from the sinus node.

This influx then depolarizes the atrioventricular node and reaches the ventricles (VDG1 marker). It also spreads to the left atrium (OG1 marker), with a significant delay in the pathology of heart failure with preserved ejection fraction, so that in the shown example, depolarization of the left atrium (OG1 marker) and of the ventricles (VDG1 marker) are substantially concurrent.

The cycle is repeated (Cycle 2), with an interval of atrial coupling D1 corresponding to sinus rhythm. The sequencing default of the left atrium occurs, with a too long interval D2 between the depolarizations of the right (marker OD2) and left (marker OG2) atria.

At the next cycle (cycle 3), in accordance with the invention, a stimulation is delivered to the left atrium (StimOG3 marker) after a period A from the previous depolarization of the left atrium (OG2 Marker). This duration is chosen to generate a predetermined prematurity PM (relative to the marker OG3' of the depolarization that would have occurred with the normal atrial coupling interval), calculated to (1) ensure that the OG3-VDG3 interval is long enough to establish a normal sequencing of the left cavities, and (2) not to change the sequencing OD3-VDG3 of the right cavities.

To do this, the device determines the durations D1 (OD1-OD2) and D2 (OD2-OG2) during cycles 1 and 2, and calculates prematurity:

$$PM = D2 - a$$

a being a time interval chosen to correspond, e.g., to the propagation delay between the sinus node and the right atrium (delay indicated by the arrow 10 in FIG. 1) so that the depolarization of the left atrium is not synchronous with that of the right atrium, but slightly delayed compared to the latter. That delay can be fixed, for example, 50 ms, or programmable. Alternatively, a may be zero if it is desirable that both atria are synchronous, or even be negative if one wants the contraction of the left atrium occurs above that of the right atrium.

This prematurity PM corresponds, as explained above, to a duration A=D1-PM counted from the previous depolarization of the left atrium (OG2 marker) before delivering of a stimulation to the left atrium (StimOG3 marker).

If a left atrial post-stimulation blanking period is applied, the preferred is a positive a interval which positions the left atrial stimulation just after the right atrial detection, thereby preventing the application of a post-stimulation blanking that would jeopardize this detection.

During the next cycle (Cycle 4) the device delivers stimulation to the left atrium (StimOG4 marker), but with an inter-atrial interval D1 corresponding to the interval OD1-OD2 that was measured in previous cycles before the left atrium is stimulated. The device then measures the interval OD3-OD4 (interval D3) and compares this interval to the interval OD1-OD2 (interval D1):

if D1=D3, this means that the atrial coupling is maintained, and that the (premature) stimulation of the left atrium in the previous cycle did not cause indirect depolarization of the right atrium;

if D3<D1, this means that prematurity is too large, and changed the depolarization of the right atrium; which is sought to be avoided.

The stimulation of the left atrium will then be suspended for one (or more) cycle(s), and the stimulation sequence will then be restarted, but with a reducing of the prematurity of a variation step (that is to say extending the duration A). This may be repeated as necessary until there is a sequence n such that the interval ODn-ODn+1=OD1-OD2.

On a regular basis, e.g. every minute, or in case of significant change in the right atrial coupling interval (interval D1 change above a threshold), the above method is repeated in order to dispose of a cycle without stimulation of the left atrium, which will serve as a reference.

Figure 4:
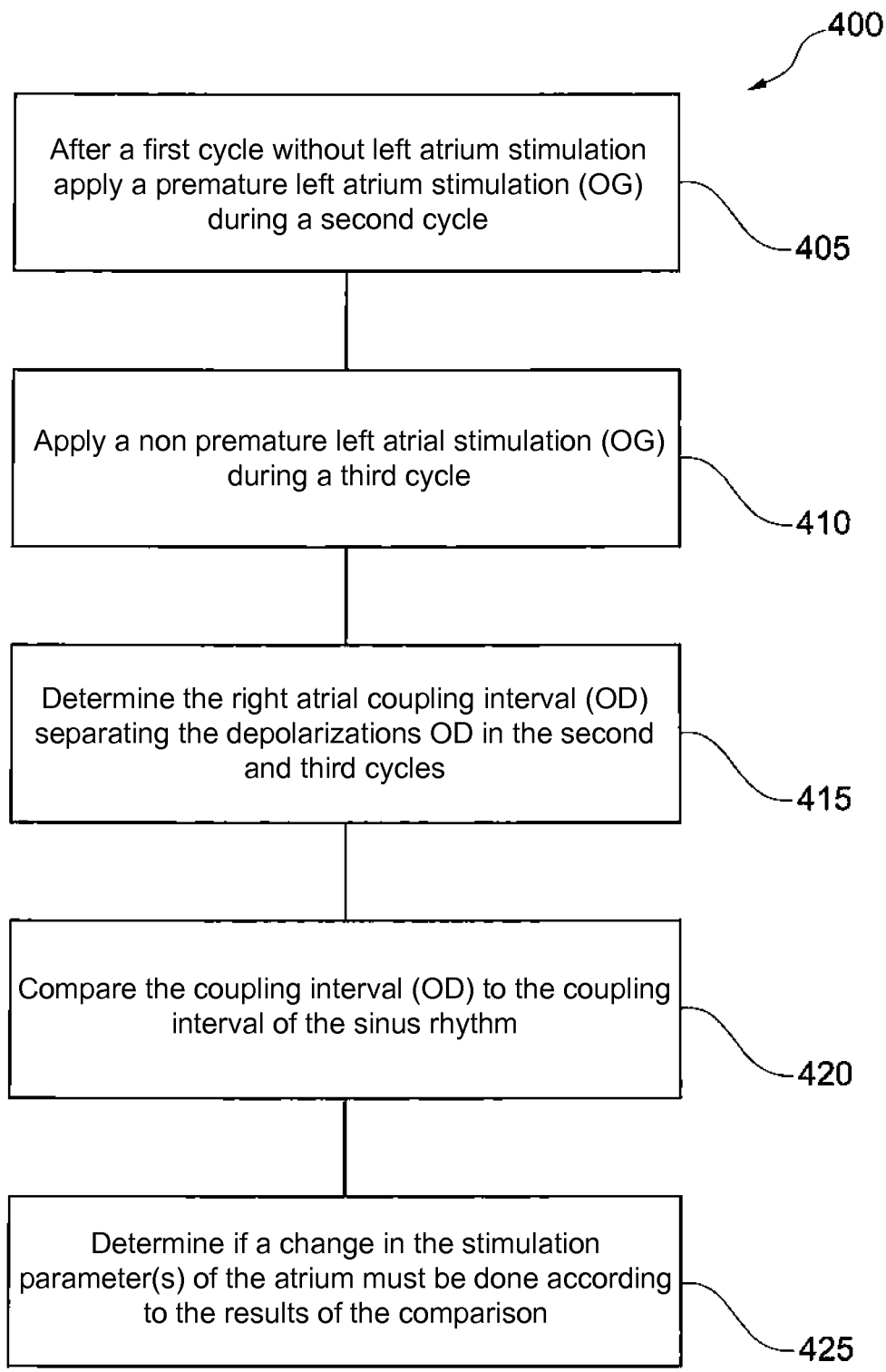
FIG. 4 is a flowchart describing the method to deliver cardiac pacing according to an embodiment of the invention.

A block diagram of a flowchart 400 of delivery of cardiac pacing according to an exemplary embodiment of the invention is shown in FIG. 4. After a first cardiac cycle in which no left atrial pacing OG is delivered, the device (e.g., an implantable medical device) delivers a premature stimulation pulse OG during the second cardiac cycle (step 405), immediately following the first cardiac cycle. The premature stimulation OG is adjusted to cause the application of a short inter-atrial coupling shorter than the sinus rhythm coupling interval.

The device then applies a not premature pacing pulse OG during a third cardiac cycle (step 410), which immediately follows the second cardiac cycle. The not premature stimulation pulse OG is adjusted so as to cause the application of an inter-atrial coupling which corresponds to the coupling interval of the sinus period.

The device then determines a right atrial coupling interval OD between the depolarizations of the right atrium in the second and third cycles (step 415). The device compares the coupling interval OD to the sinus rhythm coupling interval (step 420). Depending on the result of the comparison, the device determines if it is necessary and/or how to modify one or more parameters of the stimulation applied to the left atrium during subsequent cardiac cycles (step 425). One or more steps of the flowchart 400 may be repeated after changing of the settings, to further modify the parameters and/or to optimize the stimulation of the left atrium.

Figure 5:
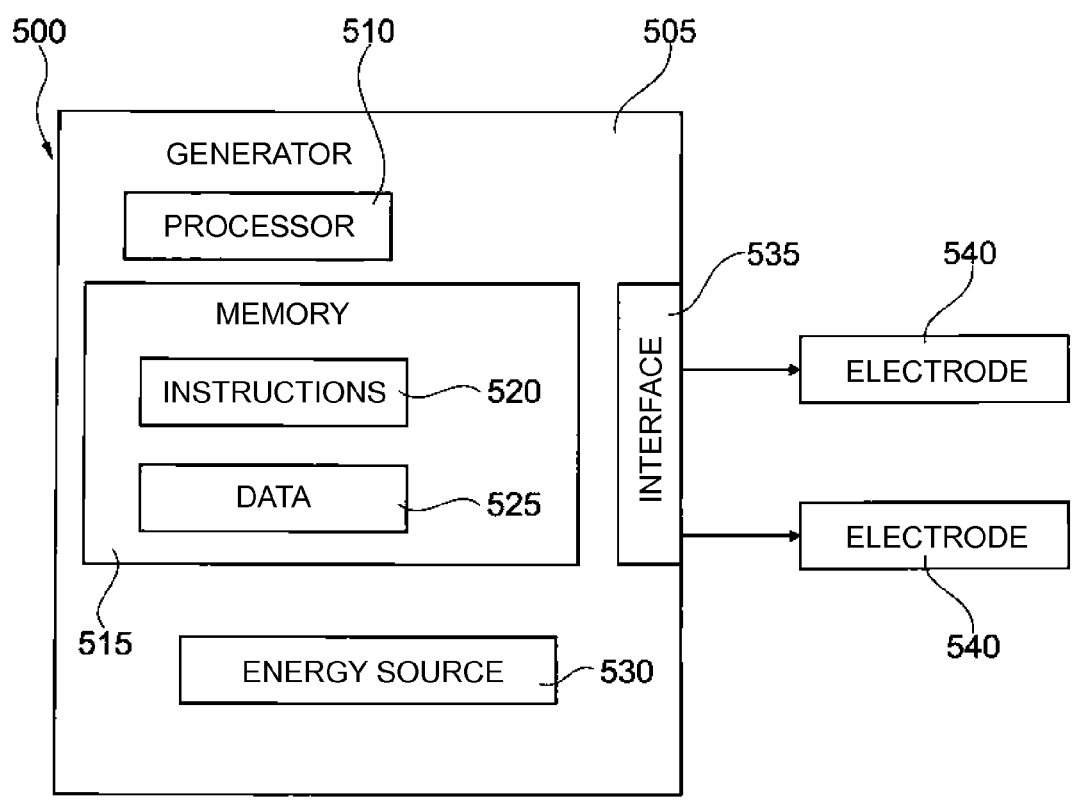
FIG. 5 is a block diagram illustrating an embodiment of an implantable medical device that can be used to implement various features presented herein.

A block diagram of an exemplary embodiment of a device 500 that can be used to implement various features described above is shown in FIG. 5. The device 500 may be an implantable medical device adapted to be implanted in a subject, e.g. a patient. The device 500 includes a generator 505 configured to generate stimulation signals to tissue, for example a cardiac tissue, nerve tissue, etc.). Detection signals can be received from one or more electrodes 540 coupled to generator 505 via wire 535 or a wireless interface. In some embodiments, the generator 505 can be connected to the electrodes 540 by cables. Also, in some embodiments the generator 505 may be connected to electrodes and include a power source such as a battery 530. In some embodiments, the generator 505 may include one or more wireless transceivers configured to allow the generator 505 to communicate wirelessly with one or more other devices (e.g., devices external to the patient). For example, a wireless transceiver may communicate with a computing device for general purpose or special purpose (e.g., a desktop computer, a tablet, etc.), particularly in a hospital or in a clinical environment for transmitting signals to and from the external computer device, for example to receive control signals configured for controlling the detection/stimulation settings for the generator 505 and/or provide data relating to the detection/stimulation to the external computing device.

The generator 505 includes a processor 510 and a memory 515. The processor 510 can be of any standard type or a processor for special purposes that may be integrated into the housing of the generator 505. The memory 515 can include any appropriate type of storage medium readable by a machine for storing machine-executable instructions 520 machine and/or other data 525. The instructions 520 can be executed by the processor 510 to implement various operations described in this paper. For example, such storage media readable by a machine may include RAM, ROM, EPROM, EEPROM, flash memory or any other means which can be used to transfer or store program code in the form of machine executable instructions or of data structures that can be read by a machine with a processor. Any combination of the above is also included in the scope of what is referred to as a storage medium readable by machine. The machines or computer-readable storage supports mentioned here do not include the temporary supports, such as signals in free field.

In some embodiments, the memory 515 may include one or more modules with instructions configured to cause the processor 510 to perform various functions such as those described above. For example, the memory 515 may include a stimulation module configured to control the generation and/or transmission of stimulation pulses (e.g. the atrial pacing pulses) to electrodes 540. The memory 515 may include a module configured to detect the information collected by the electrodes 540 and assess the response to be provided (for example, assessing the atrial coupling interval and/or comparing the right atrial coupling interval and the sinus rhythm interval). The detection unit may be configured to modify one or more parameters of the stimulation depending on this evaluation. The parameters can also be stored in the memory 515.

What is claimed is:

1. An active implantable medical device comprising:
a processor configured to:
sense a plurality of right atrial depolarizations; and
deliver a plurality of left atrial stimulation pulses according to a stimulation protocol, the stimulation protocol comprising:
detecting a first cardiac cycle without left atrial stimulation;
delivering a left atrial stimulation pulse during a second cardiac cycle subsequent to the first cardiac cycle at an inter-atrial coupling interval, wherein the inter-atrial coupling interval applied during the second cardiac cycle is shorter than a sinus rhythm coupling interval;
delivering a left-atrial stimulation pulse during a third cardiac cycle subsequent to the second cardiac cycle at an inter-atrial coupling interval corresponding to the sinus rhythm coupling interval;
determining a right atrial coupling interval between the right atrial depolarizations during the second and third cardiac cycles;
comparing the right atrial coupling interval to the sinus rhythm coupling interval; and
selectively modifying an adjustable controlling parameter according to the comparison.

2. The device of claim 1, wherein the adjustable controlling parameter is the inter-atrial coupling interval.

3. The device of claim 2, wherein, when the comparison indicates the right atrial coupling interval is less than the sinus rhythm coupling interval, the processor is further configured to modify the adjustable controlling parameter by:
changing the inter-atrial coupling interval by one step; and
delivering a left atrial stimulation pulse during a subsequent cardiac cycle at the inter-atrial coupling interval changed by one step.

4. The device of claim 1, wherein, when a predetermined event is detected, the processor is further configured to:
inhibit delivery of the left atrial stimulation pulse during at least one cardiac cycle;
measure an atrial escape interval and an inter-atrial delay for a cardiac cycle; and
store the atrial escape interval as the sinus rhythm coupling interval for determination of the inter-atrial coupling interval and the inter-atrial delay corresponding to the sinus rhythm coupling interval in subsequent cycles.

5. The device of claim 4, wherein the predetermined event is an expiration of a predetermined fixed timing interval.

6. The device of claim 4, wherein the predetermined event is a detection of a crossing of a predetermined threshold by a variation in the inter-atrial coupling interval.

7. A method for resynchronization of a contraction of heart chambers, the method comprising:
sensing a plurality of right atrial depolarizations; and
delivering a plurality of left atrial stimulation pulses according to a stimulation protocol, the stimulation protocol comprising:
detecting a first cardiac cycle without left atrial stimulation;
delivering a left atrial stimulation pulse during a second cardiac cycle subsequent to the first cardiac cycle at an inter-atrial coupling interval, wherein the inter-atrial coupling interval applied during the second cardiac cycle is shorter than a sinus rhythm coupling interval;
delivering a left-atrial stimulation pulse during a third cardiac cycle subsequent to the second cardiac cycle, at an inter-atrial coupling interval corresponding to the sinus rhythm coupling interval;

determining a right atrial coupling interval between the right atrial depolarizations during the second and third cardiac cycles;

comparing the right atrial coupling interval to the sinus rhythm coupling interval; and selectively modifying an adjustable controlling parameter according to the comparison.

8. The method of claim 7, wherein the adjustable controlling parameter is modified to cause an interval between left atrial contraction and ventricular contraction long enough to establish a normal sequencing of the left cavities of the heart while causing no change in sequencing of a right atrial contraction and ventricular contraction of the heart.

9. The method of claim 7, wherein the adjustable controlling parameter is the inter-atrial coupling interval.

10. The method of claim 9, further comprising modifying the inter-atrial coupling interval when the right atrial coupling interval is less than the sinus rhythm coupling interval.

11. The method of claim 10, wherein the modifying step comprises:

changing the inter-atrial coupling interval by one step; and delivering a left atrial stimulation pulse during a subsequent cardiac cycle at the inter-atrial coupling interval changed by one step.

12. The method of claim 7, further comprising:

detecting a predetermined event;

inhibiting delivery of the left atrial stimulation pulse during at least one cardiac cycle;

measuring an atrial escape interval and an inter-atrial delay for a cardiac cycle; and storing the atrial escape interval as the sinus rhythm coupling interval for determination of the inter-atrial coupling interval and the inter-atrial delay corresponding to the sinus rhythm coupling interval in subsequent cycles.

13. The method of claim 12, wherein the predetermined event is an expiration of a predetermined fixed timing interval.

14. The method of claim 12, wherein the predetermined event is a detection of a crossing of a predetermined threshold by a variation in the inter-atrial coupling interval.

15. The method of claim 7, wherein the left atrial stimulation pulse is premature to a naturally occurring depolarization at a sinus rhythm by a prematurity value, wherein the prematurity value is equal to an interval between a left atrial depolarization and the right atrial depolarization during the first cardiac cycle minus an interval, wherein the interval is selected so that the left atrium depolarization is not synchronous with the right atrium depolarization, but slightly delayed.

16. A cardiac resynchronization system, comprising:

a plurality of electrodes for positioning in a right atrium and a left atrium of a heart;

an implantable medical device comprising a generator, the implantable medical device structured to couple to the electrodes, the implantable medical device further comprising a processor configured to:

sense a plurality of right atrial depolarizations from the electrodes;

sense a plurality of left atrial depolarizations from the electrodes; and deliver a plurality of a left atrial stimulation pulse during a cardiac cycle following a preceding cardiac cycle with no left atrial stimulation, the left atrial stimulation pulse delivered at an inter-atrial coupling interval, wherein the inter-atrial coupling interval is shorter than a sinus rhythm coupling interval;

deliver a second left-atrial stimulation pulse during a subsequent cardiac cycle at an inter-atrial coupling interval corresponding to the sinus rhythm coupling interval;

assess a right atrial coupling interval between the right atrial depolarizations during the consecutive cardiac cycles;

compare the right atrial coupling interval to the sinus rhythm coupling interval; and determine whether to modify the inter-atrial coupling interval based on the comparison.

17. The system of claim 16, wherein the processor is further configured to modify the inter-atrial coupling interval when the right atrial coupling interval is less than the sinus rhythm coupling interval.

18. The system of claim 17, wherein the processor is further configured to modify the inter-atrial coupling interval by:

changing the inter-atrial coupling interval by one step; and delivering a left atrial stimulation pulse during a subsequent cardiac cycle at the inter-atrial coupling interval changed by one step.

19. The system of claim 16, wherein the digital processor circuits are further configured to:

detect a predetermined event;

inhibit delivery of the left atrial stimulation pulse during a cardiac cycle;

measure an atrial escape interval and an inter-atrial delay for a cardiac cycle; and store the atrial escape interval as a sinus rhythm coupling interval for determination of the inter-atrial coupling interval and the inter-atrial delay corresponding to the sinus rhythm coupling interval in subsequent cycles.

20. The system of claim 16, further comprising a ventricular lead for implantation in a right or left ventricle of the heart.

* * * * *